(12) United States Patent
Shin (10) Patent No.: US 7,005,147 B2
(45) Date of Patent: Feb. 28, 2006

(54) FATIGUE RECOVERY MEDICINE FOR CHANGING IN HEPATIC MRNA LEVELS OF STRESS-RELATED GENES

(76) Inventor: Jun-Sik Shin, 635 Sinsa-dong, Kangnam-gu, Seoul (KR)

( * ) Notice: Subject to any disclaimer, the term of this patent is extended or adjusted under 35 U.S.C. 154(b) by 196 days.

(21) Appl. No.: 10/225,728

(22) Filed: Aug. 22, 2002

(65) Prior Publication Data

US 2003/0232096 A1    Dec. 18, 2003

(30) Foreign Application Priority Data

Jun. 5, 2002    (KR) ............................... 2002-31492

(51) Int. Cl.
*A61K 35/78*    (2006.01)
(52) U.S. Cl. ...................... 424/728; 424/757; 424/764; 424/773; 424/777
(58) Field of Classification Search ................ 424/728, 424/773, 777, 757, 764
See application file for complete search history.

(56) References Cited

U.S. PATENT DOCUMENTS 6,524,627 B1 *  2/2003  Kim et al. .................. 424/741

2005/0163870 A1 *  7/2005  Chen .......................... 424/725

OTHER PUBLICATIONS

Nobakht et al J Ethnopharmacol. Dec. 2000;73(3):453-9. ABSTRACT A study on the teratogenic and cytotoxic effects of safflower extract. Nobakht et al.*

* cited by examiner

*Primary Examiner*—Herbert J. Lilling
(74) *Attorney, Agent, or Firm*—Lee, Hong, Degerman, Kang & Schmadeka (57) ABSTRACT

A fatigue recovery medicine for changing in hepatic mRNA levels of stress-related genes is disclosed. The fatigue recovery medicine for changing in hepatic mRNA levels of stress-related genes is composed of: astragali radix of 13.2% by weight, atractylodis rhizoma alba of 8.8% by weight, angelicae gigantis radix of 8.8% by weight, longanae arillus of 8.8% by weight, lycii folium of 8.8% by weight, cridii rhizoma of 6.7% by weight, hoellen of 4.4% by weight, glycyrrhizae radix of 4.4% by weight, carthami flos of 4.4% by weight, cervi parvum cornu of 4.4% by weight, crataegi fructus of 4.4% by weight, rehmanniae radix preparata of 4.4% by weight, saussureae radix of 4.4% by weight, amomi fructus of 4.4% by weight, polygony multiflori radix of 4.4% by weight, paeoniae radix alba of 4.4% by weight and ginseng radix of 4.4% by weight.

1 Claim, 9 Drawing Sheets

FATIGUE RECOVERY MEDICINE FOR CHANGING IN HEPATIC MRNA LEVELS OF STRESS-RELATED GENES

BACKGROUND OF THE INVENTION

1. Field of the Invention

The present invention relates to a fatigue recovery medicine for changing in hepatic mRNA levels of stress-related genes, and more particularly, to a fatigue recovery medicine for changing in hepatic mRNA levels of stress-related genes which contains atractylodis rhizoma alba, angelicae gigantis radix, longane arillus, lycii folium, cridii rhizoma and other medicines and is applicable to a variety of stress-related diseases such as chronic fatigue, neurasthenia, etc.

2. Description of the Related Art

As is generally known, in modern society, with multiple changes in the society, new diseases are being occurred. Among them, chronic fatigue syndrome is representative. The chronic fatigue syndrome is an illness characterized by continuous debilitating fatigue, although the lesion thereof has not been not found as cancer or AIDS.

The U.S. Centers for Disease Control defined the term "chronic fatigue syndrome" as fatigue that is severe enough to impair average daily activity for a period of at least 6 months. To overcome such chronic fatigue syndrome by drugs, a variety of medicines have been produced.

As medicines for the chronic fatigue syndrome, dietary supplements such as antiviral agent or folic acid are typical among medicines currently on the market. However, such medicines are proved to be very unsatisfactory in point of treatment effect by experiments because fatigue is not caused by undernutrition.

SUMMARY OF THE INVENTION

Accordingly, an object of the present invention is to solve the foregoing problems by providing a fatigue recovery medicine for changing in hepatic mRNA levels of stress-related genes which contains atractylodis rhizoma alba, angelicae gigantis radix, longane arillus, lycii folium, cridii rhizoma and other medicines and is applicable to a variety of stress-related diseases such as chronic fatigue, neurasthenia, etc.

To achieve the above object, there is provided a fatigue recovery medicine for changing in hepatic mRNA levels of stress-related genes in accordance with a preferred embodiment of the present invention, which is composed of: astragali radix of 13.2% by weight, atractylodis rhizoma alba of 8.8% by weight, angelicae gigantis radix of 8.8% by weight, longanae arillus of 8.8% by weight, lycii folium of 8.8% by weight, cridii rhizoma of 6.7% by weight, hoellen of 4.4% by weight, glycyrrhizae radix of 4.4% by weight, carthami flos of 4.4% by weight, cervi parvum cornu of 4.4% by weight, crataegi fructus of 4.4% by weight, rehmanniae radix preparata of 4.4% by weight, saussureae radix of 4.4% by weight, amomi fructus of 4.4% by weight, polygony multiflori radix of 4.4% by weight, paeoniae radix alba of 4.4% by weight and ginseng radix of 4.4% by weight.

BRIEF DESCRIPTION OF THE DRAWINGS

The above objects, features and advantages of the present invention will become more apparent from the following detailed description when taken in conjunction with the accompanying drawings, in which.

DETAILED DESCRIPTION OF THE PREFERRED EMBODIMENT

The present invention will now be described in detail with reference to the accompanying drawings.

A fatigue recovery medicine for changing in hepatic mRNA levels of stress-related genes in accordance with the preferred embodiment of the present invention is composed of: astragali radix of 10 to 20% by weight, atractylodis rhizoma alba of 7 to 8% by weight, angelicae gigantis radix of 7 to 8% by weight, longanae arillus of 7 to 8% by weight, lycii folium of 6 to 7% by weight, cridii rhizoma of 4 to 5% by weight, hoellen of 4 to 5% by weight, glycyrrhizae radix of 4 to 5% by weight, carthami flos of 4 to 5% by weight, cervi parvum cornu of 4 to 5% by weight, crataegi fructus of 4 to 5% by weight, rehmanniae radix preparata of 4 to 5% by weight, saussureac radix of 4 to 5% by weight, amomi fructus of 4 to 5% by weight, polygony multiflori radix of 4 to 5% by weight, paeoniae radix alba of 4 to 5% by weight and ginseng radix of 4 to 5% by weight.

More preferably, the composition of fatigue recovery medicine for changing in hepatic mRNA levels of stress-related genes is shown as in Table 1.

| Ingredient | Weight Proportion |
| --- | --- |
| Astragali radix | 13.2% by weight |
| Atractylodis rhizoma alba | 8.8% by weight |
| Angelicae gigantis radix | 8.8% by weight |
| Longanae arillus | 8.8% by weight |
| Lycii folium | 8.8% by weight |
| Cridii rhizoma | 6.7% by weight |
| Hoellen | 4.4% by weight |
| Glycyrrhizae radix | 4.4% by weight |
| Carhami flos | 4.4% by weight |
| Cervi parvum cornu | 4.4% by weight |
| Crataegi fructus | 4.4% by weight |
| Rehmanniae radix preparata | 4.4% by weight |
| Saussureae radix | 4.4% by weight |
| Amomi fructus | 4.4% by weight |
| Polygony multiflori radix | 4.4% by weight |
| Paeoniae radix alba | 4.4% by weight |
| Ginseng radix | 4.4% by weight |

The fatigue recovery medicine for changing in hepatic mRNA levels of stress-related genes in accordance with the preferred embodiment of the present invention is effective in treating chronic fatigue symptoms caused by an excessive liver activity, neurasthenia of heart, anxiety neurosis, sexual nerve weakness accompanied by the fatigue of kidney function.

The principle of the medicine is to treat terrible hardship weakness, reduce ischemia, produce sap, and increase self-recovery force.

Hereinafter, the effects of the fatigue recovery medicine for changing in hepatic mRNA levels of stress-related genes in accordance with the preferred embodiment of the present invention will be proven by various experiments.

The following is experimental data from the Center for Occupational and Environmental Health, Department of Community and Environmental Medicine, University of California with the participation of Chang Sok So, Kaizhi G. Sharman, Edward H. Sharman, and Stephen C. Bondy+.

The basal levels of expression of mRNA of 23 stressed-related genes in the livers of 5, 17, and 28 month-old female B6D2F1 mice have been measured. Seven of these genes showed measurable expression levels: Gadd45, Grp78, Hsp86, Mdm2, Sod1, and Trpm2. Dietary administration of the fatigue recovery medicine (1.0%) for 13 weeks prior to sacrifice resulted in significant modulation of expression of Gadd45, Grp78, Hsp86 and Sod1. Open field behavioral testing revealed normal age-related decline in function, but the fatigue recovery medicine had no significant effect on open field behavior.

Firstly, experiments include animal treatment, Northern Blot analysis, and statistical analyses.

[Animal Treatment]

Female B6D2F1 mice, hybrid between the C57BL/6 and DBA/2 strans from Harlan Labs (Indianapolis, Ind.), aged 5 months (young group), 17 months (middle-aged group) and 28 months (old group), were housed four per cage and were maintained on a 12 hour light/dark cycle in a temperature controlled ($20\pm1°$ C.) room. Food and water were provided ad lib to animals in each group. The pelleted minimal AIN93M basal diet (#110900, Dyets Inc., Bethlehem, Pa.) consisted of 10% sucrose, 47% corn starch, 4% casein, 4% soybean oil and 21% fiber (w/w) as well as a minimal salt and vitamin mix. For one group of mice of each age this was supplemented with 1.00% (w/w) youkgongdan (a gift from Haseng Hospital, Seoul, Korea) for 13 weeks.

[RNA Extraction]

Mice were killed by cervical dislocation; liver tissue was excised quickly and immediately frozen in liquid nitrogen and stored at $-70°$ C. Total RNA waas extracted using the TRI REAGENT Kit (Molecular Research Center, Inc., Cincinnati, Ohio), following the manufacturer's protocol. RNA concentrations were determined by absorption at 260 nm wavelength. Purity was monitored by measuring the ratio of absorbance at 260 nm to that at 280 nm.

[Northern Blot Analysis]

Aliquots of total RNA (10 $\mu$g each, as determined from absorbance at 260 nm wavelength and verified by gel ethidium bromide fluorescence intensity) were reverse-transcribed with [$\alpha$-32P]dCTP incorporated and applied to cDNA microarrays (SuperArray Inc., Betheseda, Md.) containing the 23 stress-related genes listed in Table 1. The microarrays were autoradiographed for periods varying from 8 hours to 7 days at $-70°$ C. on x-ray film (X-OMAT Ar, Kodak, and Rochester, N.Y.). A densitometer (Eagle Eye image-processor combined with DNA Scan signal analysis software, Stratagene, San Diego, Calif.) was used to quantify the signals as area-integrated optical density.

[Statistical Analyses]

Differences between groups were assessed by one-way Analysis of Variance followed by Gabriele's Test. The acceptance level of significance was $p<0.05$ using a two-tailed distribution.

(Measurement of Locomotor Activity)

During the week prior to sacrifice, mice were tested for open field locomotor activity by using a Digiscan Animal Monitor (Accuscan Inc., Columbus, Ohio). The testing apparatus consisted of an empty plastic cage (40×40×30 cm with 16 photocell detectors along two perpendicular sides of the box and 16 light-emitting diodes (LEDs) along the other two sides. Another set of 8 LEDs and detectors were mounted 7.5 cm above the floor to detect vertical rearing activity. Total distance traveled was measured rather than horizontal activity as this is a more accurate indicator of ambulatory activity. Advantages of the optical beam technique for measuring activity include: (1) Two indices reflecting exploratory activity were emphasized; i) vertical rearing behavior and ii) the difference between the time spent at cage margins and that spent in the central area of the test chamber. The test subjects are unaware of the invisible infrared light beams so that behavior is unaffected by the monitoring instrument; (2) the Digiscan is insensitive to activity outside the narrow range of optical beams, unlike proximity or vibration type sensors; and (3) the output, collected and printed with a Digiscan Analyser, is digital in nature and very repeatable. The apparatus was cleansed with detergent to remove residual odors.

Testing was conducted between 7 am and 5 pm; starting times were randomized among groups. Each animal was tested for 30 minutes at the same time of day on each of two successive days; the sum of the two values for each parameter was used. The animals were introduced into the cage for the first time on day 1.

[Experimental Results]

| Name | Abbreviation | Protein function |
|---|---|---|
| Activated transcription factor | ATF-2 | DNA-binding protein |
| BC1-related X protein | Bax | Overexpression causes opoptosis. |
| FBJ murine osteosarcoma virus oncogene homolog | c-fos | Cell activity index; transcription factor, direct early gene product |
| Jun oncogene | c-jun | Direct early gene product |
| myelocytomatosis | c-myc | DNA-binding transcription factor; upregulated in human cancers; apoptosis |
| α-Crystalline B | Cryab | Structural protein |
| Early growth reaction | egr-1 | Transcription regulation |
| Growth arrest and DNA damage inducible 45 alpha | Gadd45 | ribosome constituent; protein biosynthesis |
| Growth arrest and DNA damage inducible 45 beta | Gadd45β | Ribosome constituent; protein biosynthesis; apoptosis |
| Glyceraldehyde-3-phosphate dehydrogenase | GAPDH | Metabolic enzyme; corresponding action |
| Glucose regulated protein 78KD | Grp78 | Heat shock protein; ATP-binding protein |
| Heat shock factor 1 | Hsf1 | Transcription factor; heat shock reaction |
| Heat shock protein 25 | hsp25 | Maintain appropriate form of protein |
| Heat shock protein 86 | hsp86 | Maintain appropriate form of protein |
|  | IκBα | Suppress NFκB nuclear transcription |
| Inducible nitric oxide synthase | iNOS | Generate nitric oxide |
| Mice double minute chromosome | Mdm2 | Overexpression of oncogene causes tumor |
| Mitogen activated protein Kinase | MκK4 | Protein kinase |
| Nuclear factor κ B | NF κ B1 | Stress and inflammation-related transcription factor |
| Wild-type p53 activated protein-1 | p21$^{Waf1}$ | Relate to DNA damage, suppress progression of cell cycle, apoptosis |
| Mitogen activated protein kinase | P38$^{MAPk}$ | Protein kinase |
| Transformation-related protein 53 | P53 | Transcription factor; apoptosis repressor protein |
| Cu-Zn overoxidation dismutase | SOD1 | Antioxidant enzyme protecting cells from active oxygen group |
| Testosterone-repressed prostatic message-2 | TRPM2 | Apoptotic gene product; upregulated in tumors |

Table 2 shows a gene list analyzed by hybridization of cDNA microarrays. Genes with measurable expression levels are highlighted in gray.

Figure 1:
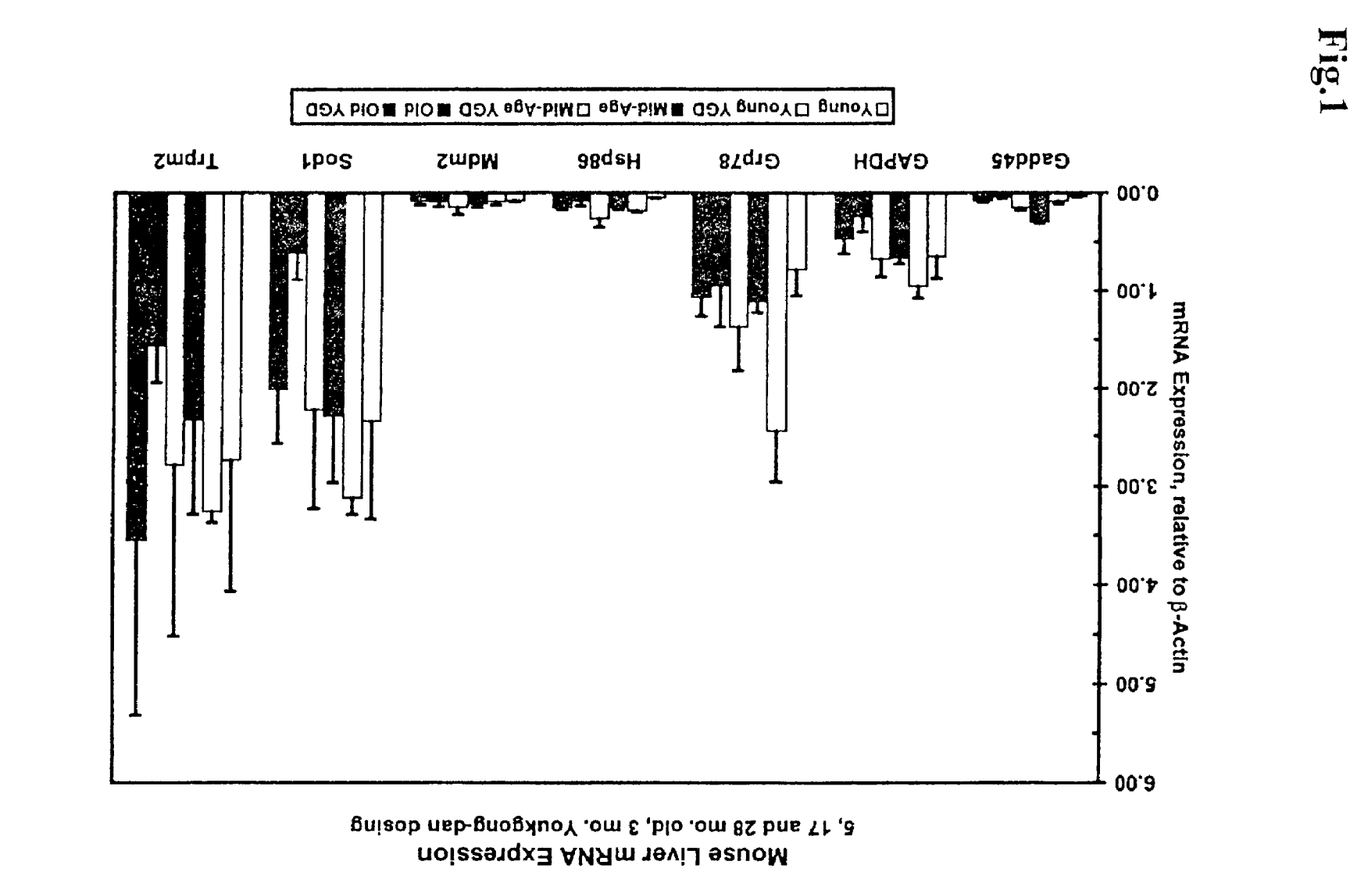
FIG. 1 is a view of densitometrically quantitated mRNA expression levels of 7 stress-related genes in the livers of mice aged 5 months (young group), 17 months (middle-aged group) and 28 months (old group) that were fed with a fatigue recovery medicine for changing in hepatic mRNA levels of stress-related genes in accordance with a preferred embodiment of the present invention.

Expression levels of seven genes were detectable; levels of the remaining genes were too low to measure with sufficient accuracy. The results are tabulated in Table 3 and displayed in FIG. 1. FIG. 1 is a view of densitometrically quantitated mRNA expression levels of 7 stress-related genes in the livers of mice aged 5 months (young group), 17 months (middle-aged group) and 28 months (old group) that were fed with a fatigue recovery medicine for changing in hepatic mRNA levels of stress-related genes in accordance with a preferred embodiment of the present invention.

TABLE 3

| Gene list | Young Control | Young Youkgong-dan | Middle-aged Control | Middle-aged Youkgong-dan | Old Control | Old Youkgong-dan |
|---|---|---|---|---|---|---|
| α-Crystallin B | 0.034 | 0.060 | 0.086 | 0.035 | 0.031 | 0.050 |
| Atf2 | 0.000 | 0.000 | 0.082 | 0.009 | 0.014 | 0.000 |
| β-Actin | 1.000 | 1.000 | 1.000 | 1.000 | 1.000 | 1.000 |
| Bax | 0.015 | 0.047 | 0.071 | 0.069 | 0.028 | 0.026 |
| c-Fos | 0.000 | 0.000 | 0.011 | 0.015 | 0.003 | 0.000 |
| c-Jun | 0.038 | 0.000 | 0.036 | 0.000 | 0.010 | 0.000 |
| c-Myc | 0.011 | 0.000 | 0.049 | 0.000 | 0.005 | 0.000 |
| Egr1 | 0.000 | 0.000 | 0.019 | 0.000 | 0.020 | 0.018 |
| Gadd45 | 0.036 | 0.080 | 0.293 | 0.147 | 0.043 | 0.080 |
| Gadd45β | 0.000 | 0.022 | 0.027 | 0.007 | 0.006 | 0.008 |
| GAPDH | 0.650 | 0.954 | 0.666 | 0.677 | 0.243 | 0.466 |
| Grp78 | 0.785 | 2.449 | 1.110 | 1.364 | 0.950 | 1.066 |
| Hsf1 | 0.000 | 0.029 | 0.032 | 0.018 | 0.022 | 0.000 |
| Hsp25 | 0.032 | 0.000 | 0.032 | 0.023 | 0.006 | 0.009 |
| Hsp86 | 0.051 | 0.180 | 0.147 | 0.260 | 0.083 | 0.147 |
| ixBa | 0.044 | 0.051 | 0.074 | 0.034 | 0.036 | 0.015 |
| iNos | 0.009 | 0.000 | 0.011 | 0.015 | 0.003 | 0.000 |
| Jnkk1 | 0.041 | 0.071 | 0.073 | 0.090 | 0.024 | 0.015 |
| Mdm2 | 0.078 | 0.087 | 0.113 | 0.146 | 0.088 | 0.082 |
| NFκB1 | 0.033 | 0.027 | 0.049 | 0.070 | 0.030 | 0.015 |
| p21$^{waf1}$ | 0.000 | 0.000 | 0.007 | 0.015 | 0.047 | 0.000 |
| p38$^{mapk}$ | 0.000 | 0.000 | 0.038 | 0.000 | 0.046 | 0.000 |
| p53 | 0.000 | 0.000 | 0.019 | 0.000 | 0.015 | 0.000 |

TABLE 3-continued

| Gene list | Young Control | Young Youkgong-dan | Middle-aged Control | Middle-aged Youkgong-dan | Old Control | Old Youkgong-dan |
|---|---|---|---|---|---|---|
| Sod1 | 2.350 | 3.125 | 2.297 | 2.229 | 0.617 | 2.015 |
| Trpm2 | 2.750 | 3.271 | 2.339 | 2.797 | 1.564 | 3.557 |

In Table 3, Youkgongdan refers to another name of the fatigue recovery medicine for changing in hepatic mRNA levels of stress-related genes. Table 3 involves young control group, young youkgongdan group, middle-aged control group, middle-aged Youkgongdan group, old control group and old Youkgongdan group. Control indicates the group not fed with Youkgongdan and Youkgongdan group indicates the group fed with Youkgongdan.

Figure 2:
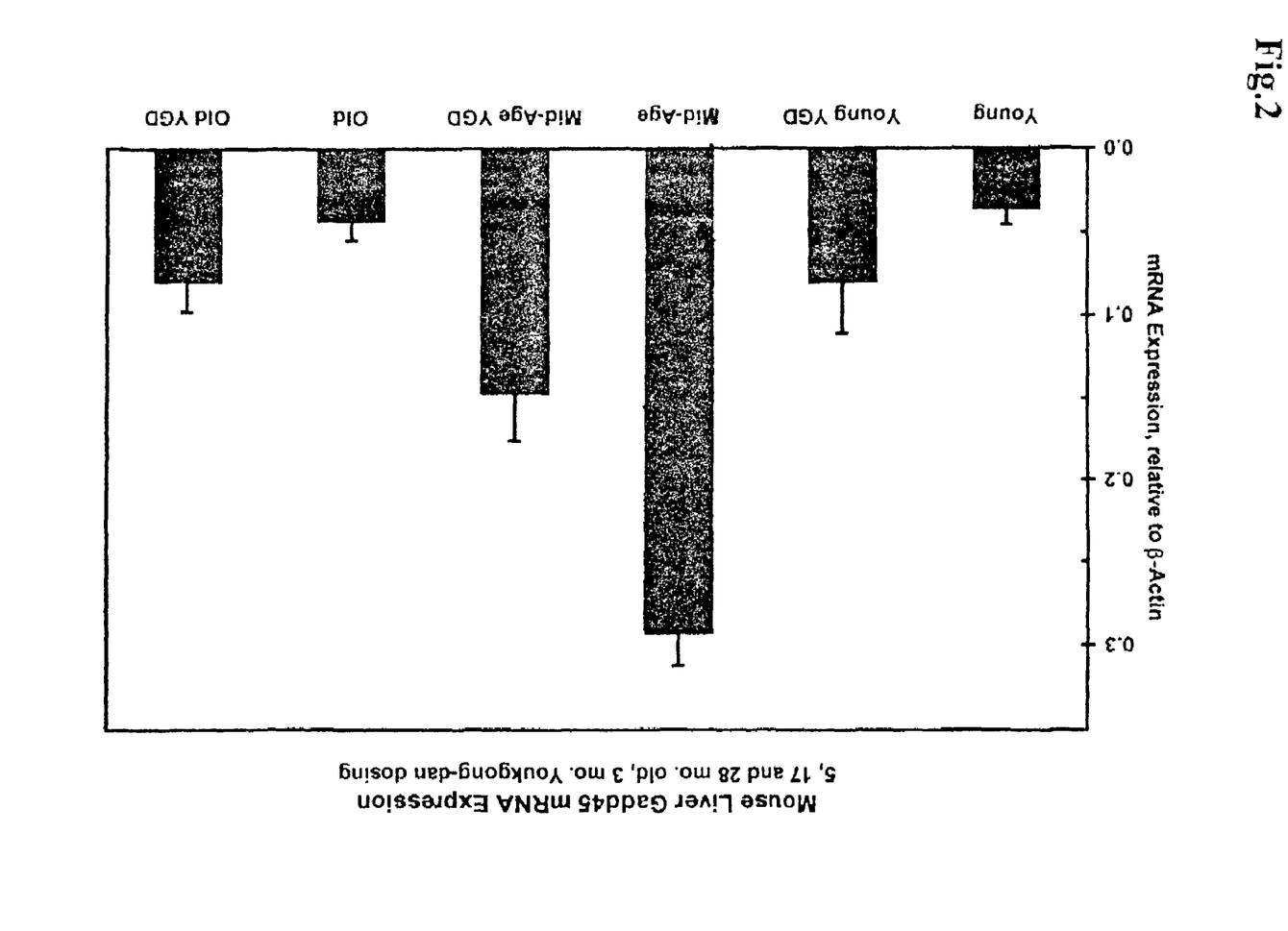
FIG. 2 is a view of densitometrically quantitated Gadd45 mRNA expression levels of the livers of mice aged 5 months (young group), 17 months (middle-aged group) and 28 months (old group) that were fed with the fatigue recovery medicine for changing in hepatic mRNA levels of stress-related genes in accordance with the preferred embodiment of the present invention.

Expression levels of Gadd45, the protein product of which is important in protein biosynthesis, were similar in young and old animals, but elevated in middle age (FIG. 2). FIG. 2 is a view of densitometrically quantitated Gadd45 mRNA expression levels of the livers of mice aged 5 months (young group), 17 months (middle-aged group) and 28 months (old group) that were fed with the fatigue recovery medicine for changing in hepatic mRNA levels of stress-related genes in accordance with the preferred embodiment of the present invention. The fatigue recovery medicine increased the Gadd45 expression in young and old animals, but greatly decreased it in middle-aged animals.

Figure 3:
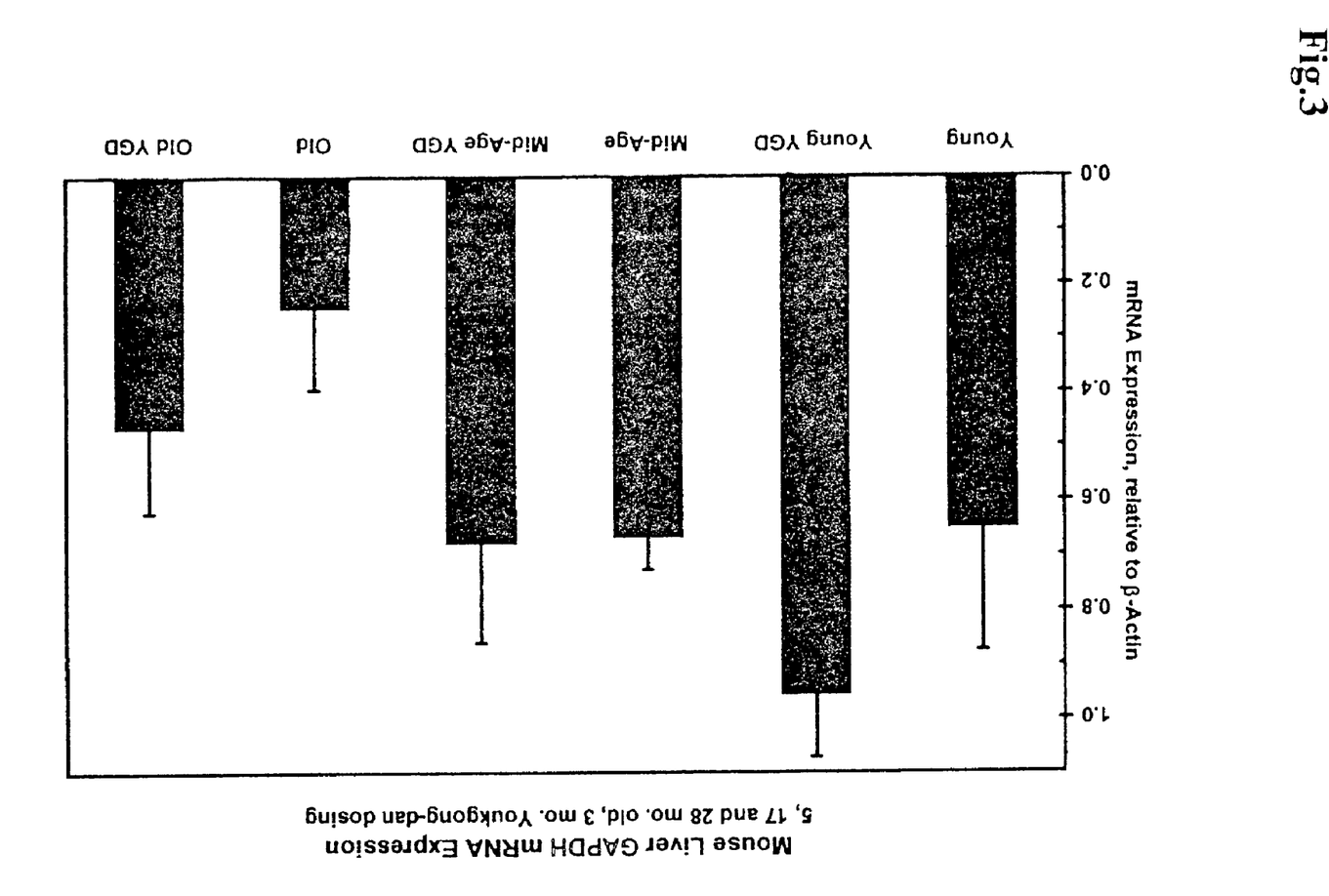
FIG. 3 is a view of densitometrically quantitated GAPDH mRNA expression levels of the livers of mice aged 5 months (young group), 17 months (middle-aged group) and 28 months (old group) that were fed with the fatigue recovery medicine for changing in hepatic mRNA levels of stress-related genes in accordance with the preferred embodiment of the present invention.

Expression levels of GAPDH, the protein product of which is important in sugar metabolism, were similar in young and middle-aged animals, but lowered in old animals (FIG. 3). The fatigue recovery medicine had no significant effect on GAPDH expression, although there was a tendency to increase its expression in young and old animals.

FIG. 3 is a view of densitometrically quantitated GAPDH mRNA expression levels of the livers of mice aged 5 months (young group), 17 months (middle-aged group) and 28 months (old group) that were fed with the fatigue recovery medicine for changing in hepatic mRNA levels of stress-related genes in accordance with the preferred embodiment of the present invention.

Figure 4:
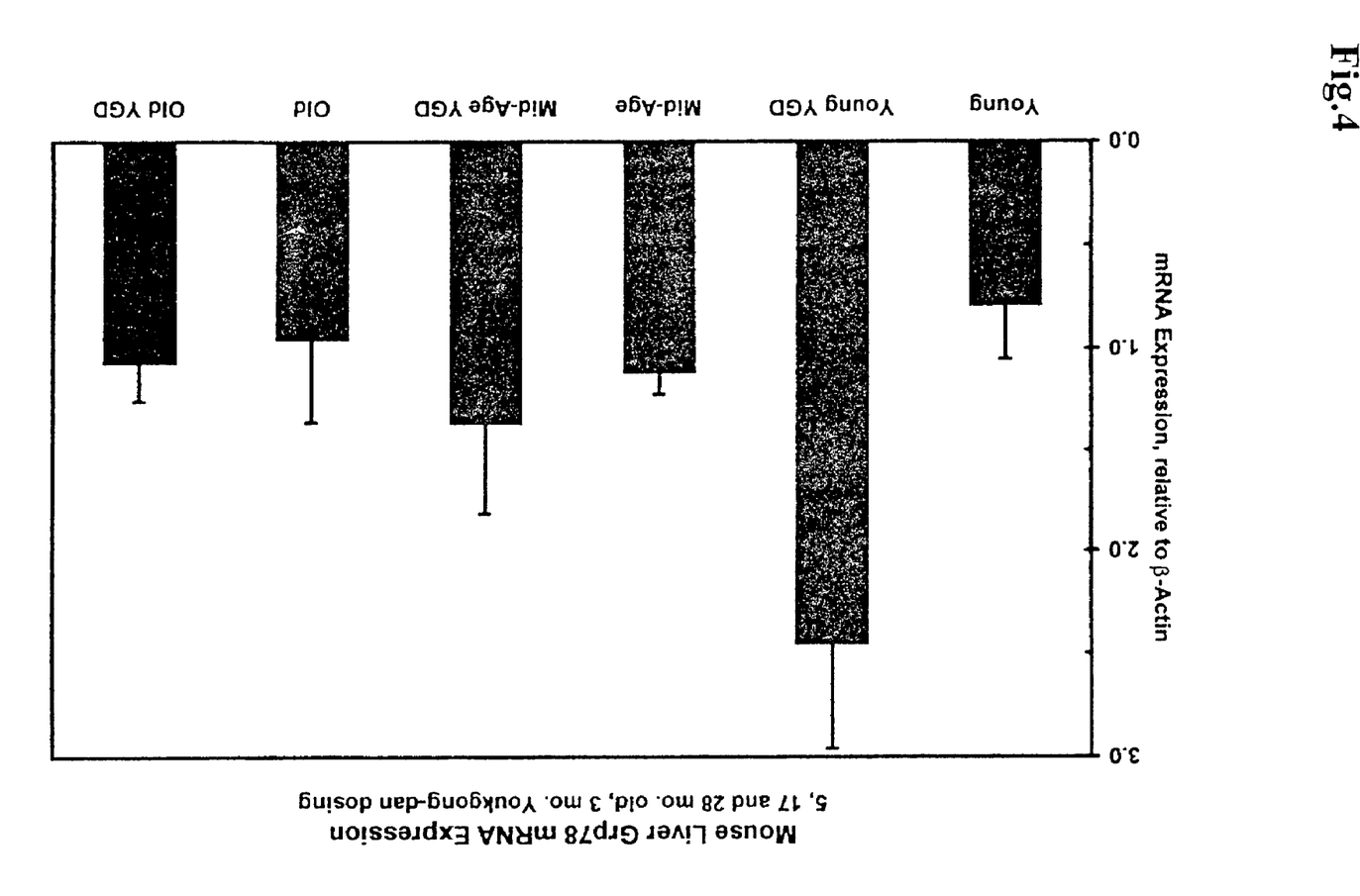
FIG. 4 is a view of densitometrically quantitated Grp78 mRNA expression levels of the livers of mice aged 5 months (young group), 17 months (middle-aged group) and 28 months (old group) that were fed with the fatigue recovery medicine for changing in hepatic mRNA levels of stress-related genes in accordance with the preferred embodiment of the present invention.

Expression levels of Grp78, which is translated into a heat shock protein, were unaffected by age (FIG. 4). The fatigue recovery medicine significantly raised Grp78 expression in young animals, but did not affect its levels in the two older groups.

FIG. 4 is a view of densitometrically quantitated Grp78 mRNA expression levels of the livers of mice aged 5 months (young group), 17 months (middle-aged group) and 28 months (old group) that were fed with the fatigue recovery medicine for changing in hepatic mRNA levels of stress-related genes in accordance with the preferred embodiment of the present invention.

Figure 5:
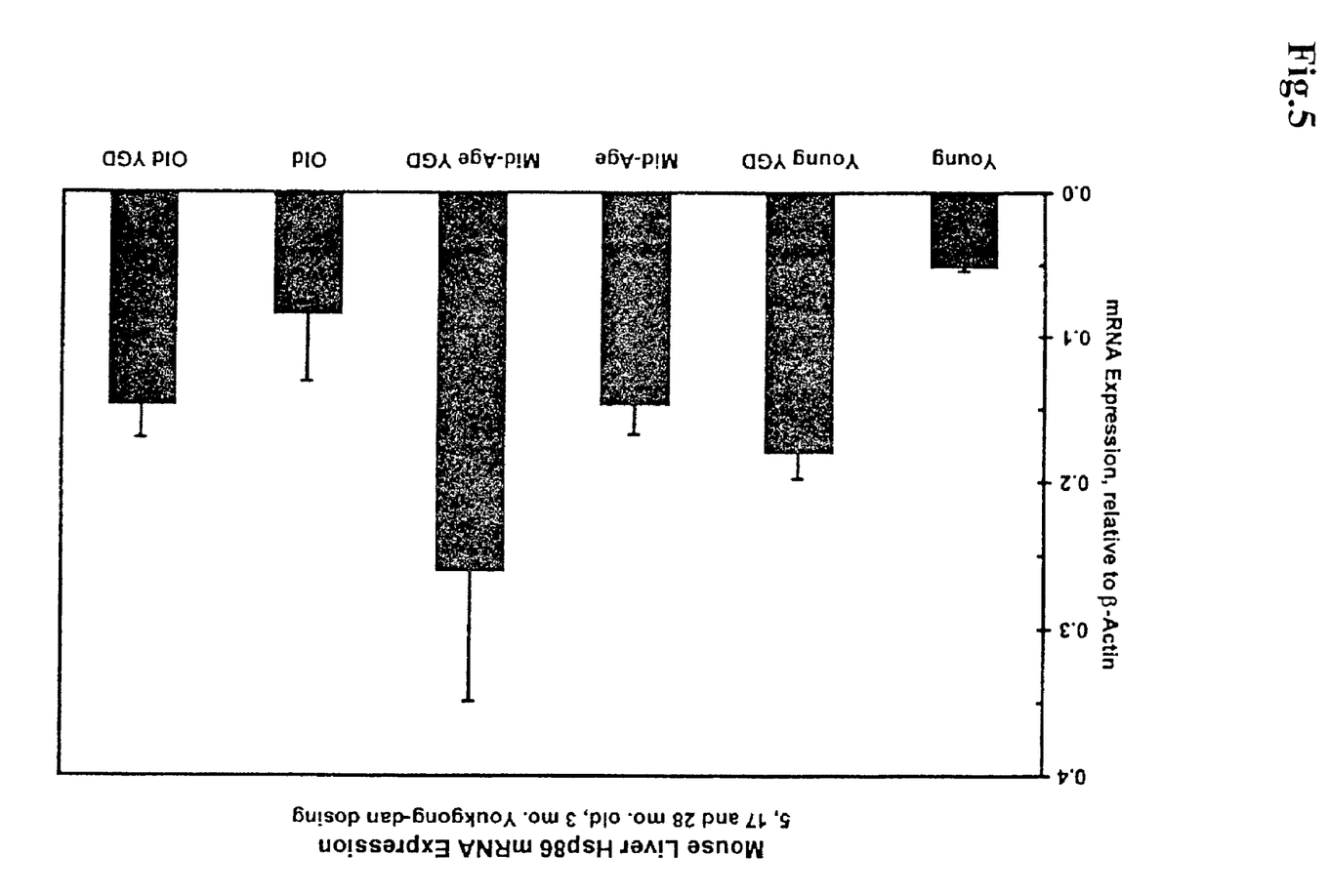
FIG. 5 is a view of densitometrically quantitated Hsp86 mRNA expression levels of the livers of mice aged 5 months (young group), 17 months (middle-aged group) and 28 months (old group) that were fed with the fatigue recovery medicine for changing in hepatic mRNA levels of stress-related genes in accordance with the preferred embodiment of the present invention.

Expression levels of Hsp86, which is translated into a heat shock protein, were significantly higher in middle-aged animals compared to young (FIG. 5). The fatigue recovery medicine significantly raised Hsp86 expression in young animals, and there was a tendency for it to increase levels of this chaperone in the two older groups.

FIG. 5 is a view of densitometrically quantitated Hsp86 mRNA expression levels of the livers of mice aged 5 months (young group), 17 months (middle-aged group) and 28 months (old group) that were fed with the fatigue recovery medicine for changing in hepatic mRNA levels of stress-related genes in accordance with the preferred embodiment of the present invention.

Figure 6:
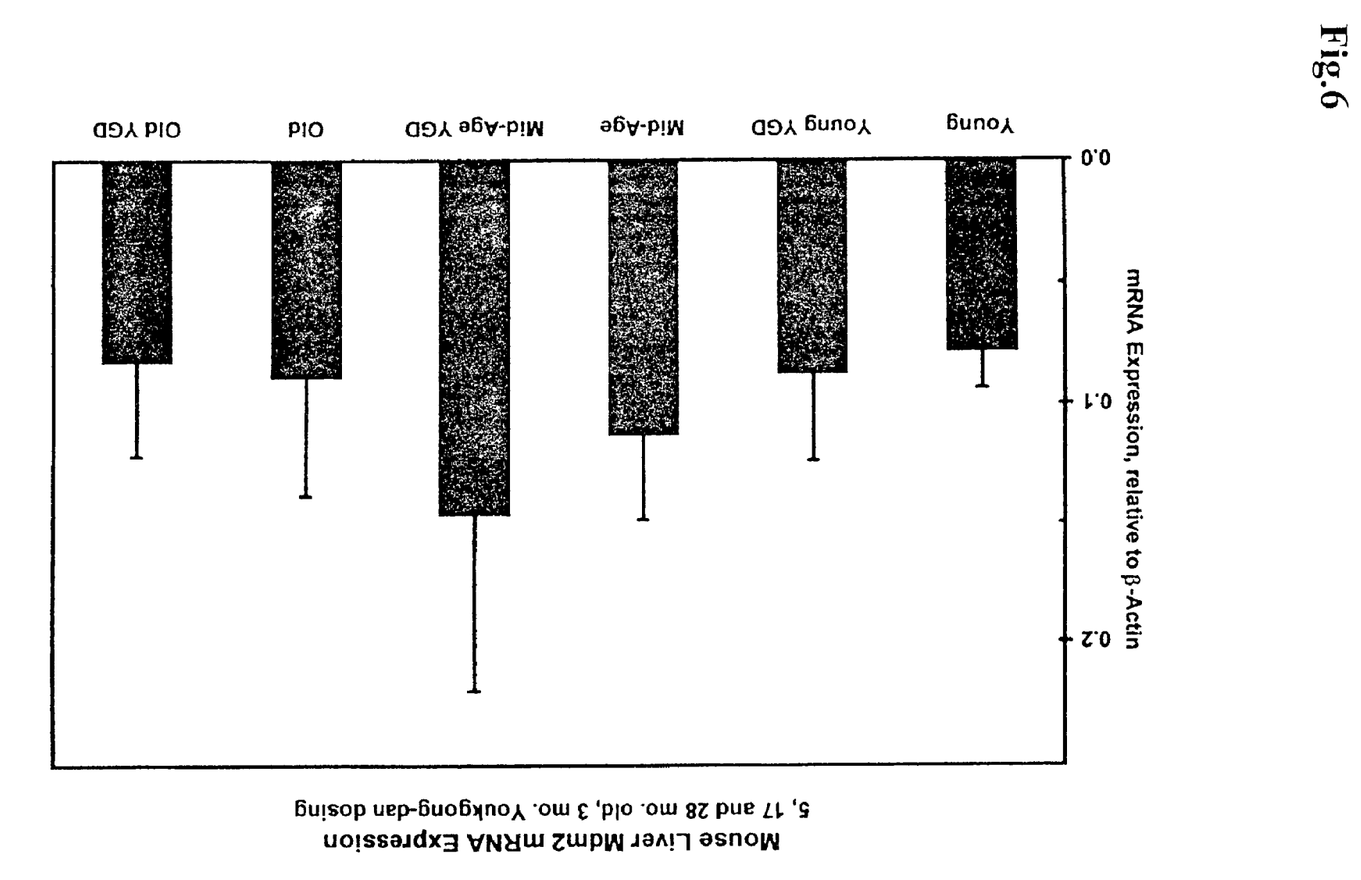
FIG. 6 is a view of densitometrically quantitated Mdm2 mRNA expression levels of the livers of mice aged 5 months (young group), 17 months (middle-aged group) and 28 months (old group) that were fed with the fatigue recovery medicine for changing in hepatic mRNA levels of stress-related genes in accordance with the preferred embodiment of the present invention.

FIG. 6 is a view of densitometrically quantitated Mdm2 mRNA expression levels of the livers of mice aged 5 months (young group), 17 months (middle-aged group) and 28 months (old group) that were fed with the fatigue recovery medicine for changing in hepatic mRNA levels of stress-related genes in accordance with the preferred embodiment of the present invention.

Figure 7:
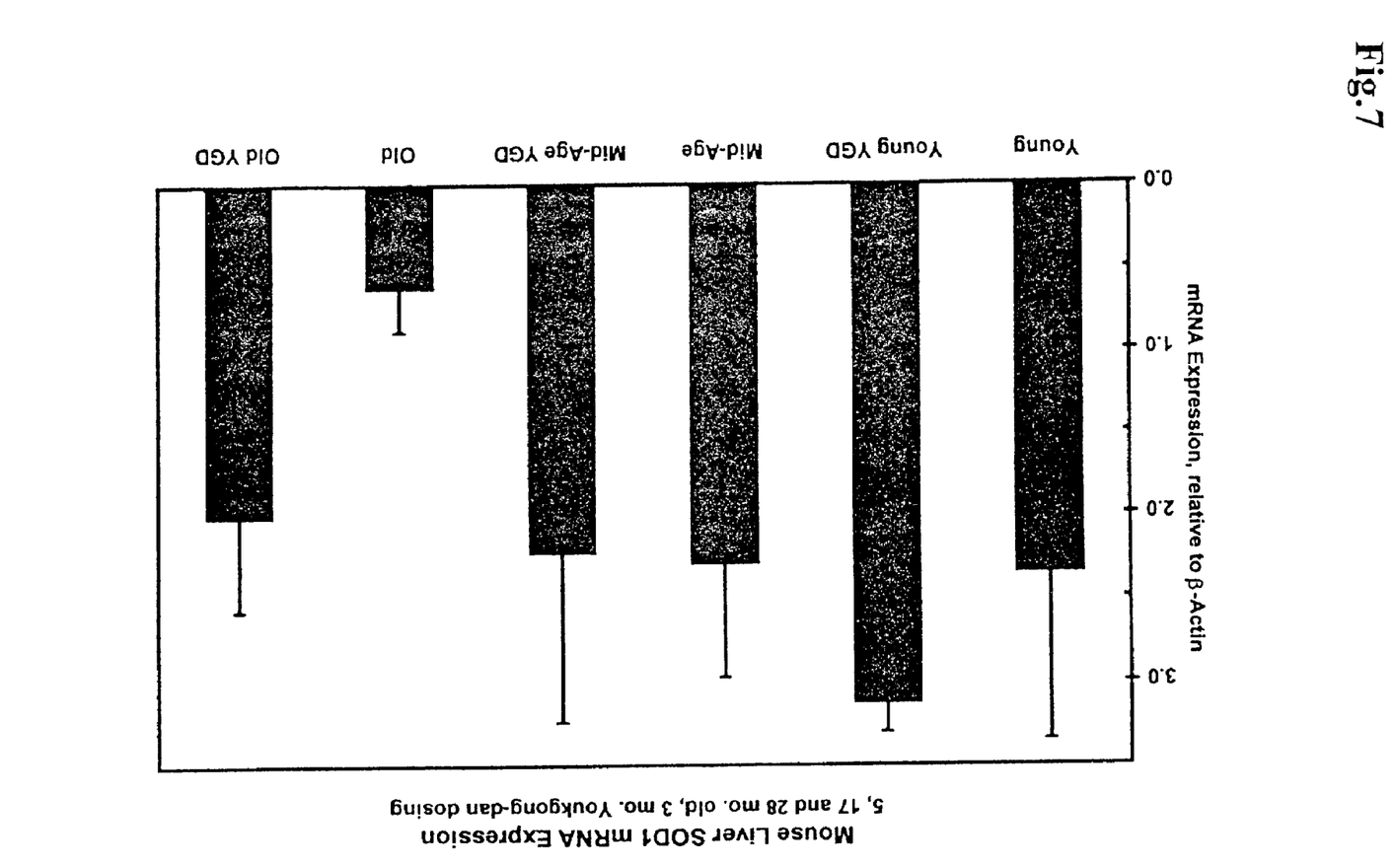
FIG. 7 is a view of densitometrically quantitated SOD1 mRNA expression levels of the livers of mice aged 5 months (young group), 17 months (middle-aged group) and 28 months (old group) that were fed with the fatigue recovery medicine for changing in hepatic mRNA levels of stress-related genes in accordance with the preferred embodiment of the present invention.

FIG. 7 is a view of densitometrically quantitated SOD1 mRNA expression levels of the livers of mice aged 5 months (young group), 17 months (middle-aged group) and 28 months (old group) that were fed with the fatigue recovery medicine for changing in hepatic mRNA levels of stress-related genes in accordance with the preferred embodiment of the present invention.

Expression levels of SOD1, the protein product of which is an important antioxidant enzyme and protector against ROS damage, were significantly lower in old animals compared to young and middle-aged (FIG. 7). The fatigue recovery medicine significantly raised SOD1 expression in old animals; although there was also a tendency for it to increase SOD1 levels in young animals also, it had no effect on middle-aged animal levels.

Figure 8:
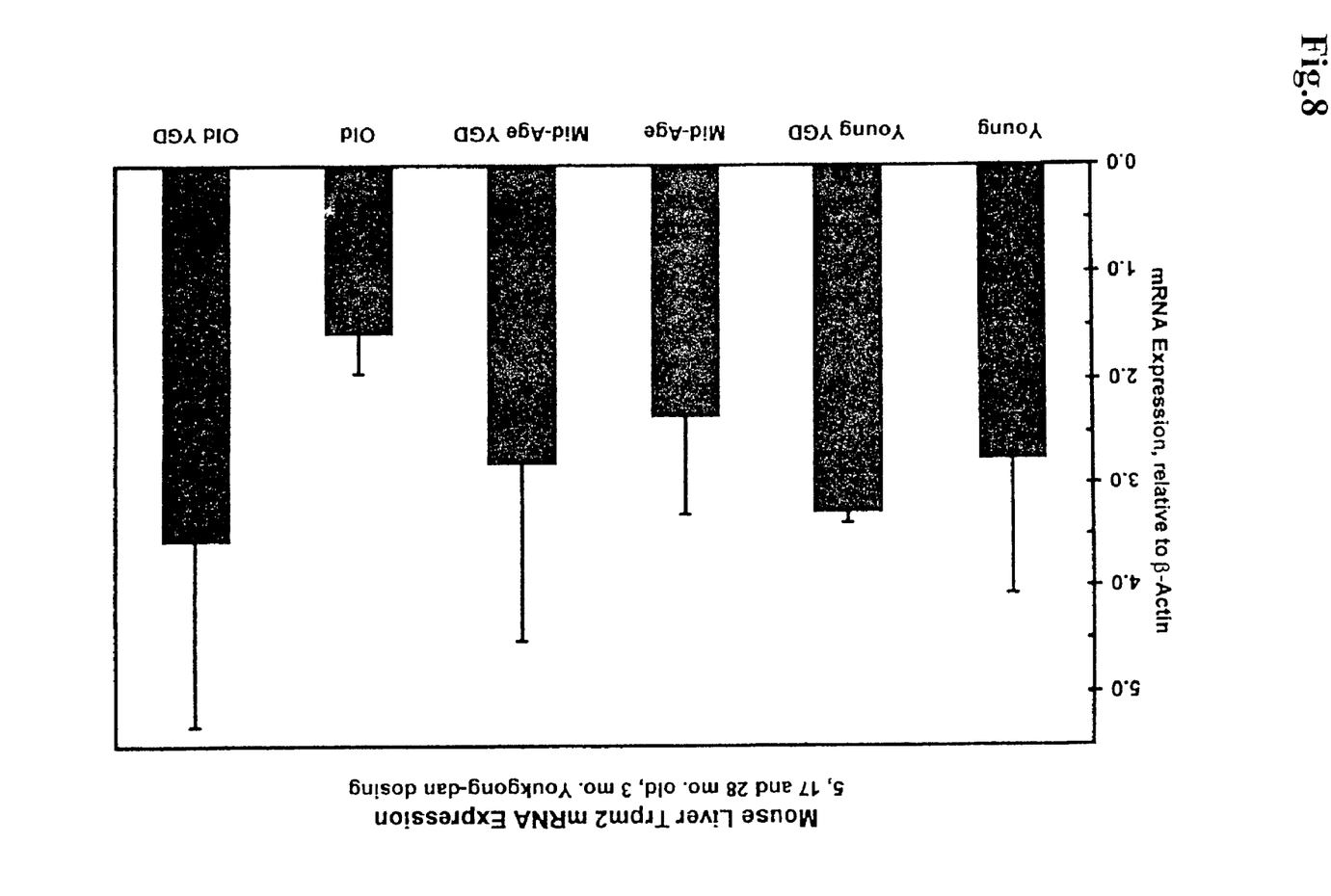
FIG. 8 is a view of densitometrically quantitated Trpm2 mRNA expression levels of the livers of mice aged 5 months (young group), 17 months (middle-aged group) and 28 months (old group) that were fed with the fatigue recovery medicine for changing in hepatic mRNA levels of stress-related genes in accordance with the preferred embodiment of the present invention.

FIG. 8 is a view of densitometrically quantitated Trpm2 mRNA expression levels of the livers of mice aged 5 months (young group), 17 months (middle-aged group) and 28 months (old group) that were fed with the fatigue recovery medicine for changing in hepatic mRNA levels of stress-related genes in accordance with the preferred embodiment of the present invention.

Trp2 expression levels are upregulated in tumors; its protein product is involved in apoptosis. There was a tendency for expression levels of Trpm2 to decrease with age. The fatigue recovery medicine tended to raise Trpm2 expression levels in animals of all ages; this tendency approached statistical significance in old animals (FIG. 8).

Open field locomotor behavior data are given in Tables 4a and 4b.

TABLE 4a

Group Y-1 Mouse Behavior Monitor Raw Data
Digiscan Animal Activity Monitor
Model RXYZCM(16), Omnitech Electronics, Columbus, OH

| Group | Day | Mouse I.D. | YC-1U | YC-28 | YC-3R | YC-4BR | YC-5RB | MC-1U | MC-28 |
|---|---|---|---|---|---|---|---|---|---|
| | 1 | Person Date | Ed Dec. 4, | Ed Dec. 4, | Ed Dec. 5, | Ed Dec. 5, | Ed Dec. 5, | Ed Dec. 4, | Ed Dec. 4, |

TABLE 4a-continued

Group Y-1 Mouse Behavior Monitor Raw Data
Digiscan Animal Activity Monitor
Model RXYZCM(16), Omnitech Electronics, Columbus, OH

|         |                              | 2001  | 2001  | 2001  | 2001  | 2001  | 2001  | 2001  |
|---------|------------------------------|-------|-------|-------|-------|-------|-------|-------|
|         | Start Time                   | 10:43 | 14:13 | 10:02 | 12.56 | 16:21 | 11:18 | 14:54 |
|         | Interval                     | 1     | 1     | 1     | 1     | 1     | 1     | 1     |
| Control | Horizontal Activity          | 5320  | 8172  | 7765  | 7604  | 5813  | 6147  | 6373  |
|         | Total Distance (cm)          | 3794  | 4855  | 6012  | 5688  | 3665  | 4175  | 4094  |
|         | No. of Movements             | 241   | 383   | 425   | 382   | 309   | 364   | 413   |
|         | Movement Time (sec)          | 355   | 465   | 491   | 476   | 396   | 427   | 449   |
|         | Rest Time (sec)              | 1449  | 1343  | 1317  | 1330  | 1410  | 1379  | 1360  |
|         | Vertical Activity            | 331   | 554   | 757   | 763   | 282   | 490   | 403   |
|         | No. of Vertical Movements    | 125   | 172   | 269   | 209   | 97    | 168   | 147   |
|         | Vertical Time (sec)          | 180   | 273   | 310   | 327   | 184   | 224   | 177   |
|         | Stereotypy Counts            | 1803  | 4090  | 2673  | 3279  | 2220  | 2501  | 2718  |
|         | No. of Stereotypy            | 221   | 282   | 257   | 273   | 287   | 258   | 284   |
|         | Stereotypy Time (sec)        | 204   | 402   | 272   | 315   | 253   | 268   | 321   |
|         | Clockwise Revolutions        | 12    | 16    | 15    | 13    | 12    | 22    | 14    |
|         | Anticlockwise Revolutions    | 15    | 14    | 19    | 27    | 15    | 6     | 15    |
|         | Margin Time (sec)            | 1645  | 1547  | 1519  | 1473  | 1598  | 1385  | 1362  |
|         | Center Time (sec)            | 154   | 252   | 281   | 328   | 203   | 414   | 437   |
|         | Left Front Corner Time (sec) | 319   | 147   | 320   | 235   | 296   | 280   | 254   |
|         | Right Front Corner Time (sec)| 287   | 160   | 176   | 256   | 466   | 194   | 94    |
|         | Left Rear Corner Time (sec)  | 245   | 166   | 202   | 223   | 101   | 147   | 120   |
|         | Right Rear Corner Time (sec) | 165   | 420   | 167   | 182   | 190   | 116   | 106   |
|         | Comments                     |       |       |       |       |       |       |       |

| Group   | Day | Mouse I.D.                   | MC-3R | MC-4BR | MC-5RB | OC-1U | OC-2B | OC-3R |
|---------|-----|------------------------------|-------|--------|--------|-------|-------|-------|
|         |     | Person                       | Ed    | Ed     | Ed     | Ed    | Ed    | Ed    |
|         | 1   | Date                         | Dec. 5, 2001 | Dec. 5, 2001 | Dec. 5, 2001 | Dec. 4, 2001 | Dec. 5, 2001 | Dec. 5, 2001 |
|         |     | Start Time                   | 9:27  | 12:22  | 15:14  | 11:53 | 10:38 | 15:47 |
|         |     | Interval                     | 1     | 1      | 1      | 1     | 1     | 1     |
| Control |     | Horizontal Activity          | 7087  | 7125   | 6017   | 6721  | 5996  | 2226  |
|         |     | Total Distance (cm)          | 5173  | 4226   | 4180   | 5524  | 5831  | 918   |
|         |     | No. of Movements             | 443   | 389    | 320    | 365   | 384   | 158   |
|         |     | Movement Time (sec)          | 505   | 456    | 464    | 534   | 553   | 131   |
|         |     | Rest Time (sec)              | 1303  | 1351   | 1341   | 1272  | 1253  | 1572  |
|         |     | Vertical Activity            | 595   | 545    | 580    | 310   | 490   | 25    |
|         |     | No. of Vertical Movements    | 190   | 191    | 162    | 122   | 163   | 14    |
|         |     | Vertical Time (sec)          | 242   | 287    | 285    | 139   | 167   | 13    |
|         |     | Stereotypy Counts            | 2592  | 3416   | 2073   | 2564  | 3037  | 845   |
|         |     | No. of Stereotypy            | 260   | 306    | 240    | 256   | 283   | 159   |
|         |     | Stereotypy Time (sec)        | 260   | 385    | 232    | 294   | 315   | 152   |
|         |     | Clockwise Revolutions        | 13    | 6      | 3      | 21    | 17    | 5     |
|         |     | Anticlockwise Revolutions    | 22    | 20     | 20     | 15    | 27    | 2     |
|         |     | Margin Time (sec)            | 1394  | 1520   | 1562   | 1391  | 1226  | 1769  |
|         |     | Center Time (sec)            | 405   | 279    | 207    | 408   | 573   | 30    |
|         |     | Left Front Corner Time (sec) | 148   | 226    | 158    | 228   | 205   | 607   |
|         |     | Right Front Corner Time (sec)| 151   | 235    | 400    | 164   | 92    | 780   |
|         |     | Left Rear Corner Time (sec)  | 160   | 201    | 119    | 153   | 143   | 27    |
|         |     | Right Rear Corner Time (sec) | 198   | 205    | 276    | 162   | 220   | 38    |
|         |     | Comments                     |       |        |        |       |       | cancer|

| Group        | Day | Mouse I.D.                   | YK-1U | YK-2B | YK-3R | YK-4BR | YK-5RB | MK-1U |
|--------------|-----|------------------------------|-------|-------|-------|--------|--------|-------|
|              |     | Person                       | Ed    | Ed    | Ed    | Ed     | Ed     | Ed    |
|              | 1   | Date                         | Dec. 4, 2001 | Dec. 4, 2001 | Dec. 5, 2001 | Dec. 5, 2001 | Dec. 5, 2001 | Dec. 4, 2001 |
|              |     | Start Time                   | 12:27 | 16:03 | 8:52  | 11:14  | 14:04  | 13:38 |
|              |     | Interval                     | 1     | 1     | 1     | 1      | 1      | 1     |
| Youkgong-dan |     | Horizontal Activity          | 7990  | 6787  | 7321  | 7067   | 7256   | 6015  |
| 10 gm/kg     |     | Total Distance (cm)          | 5778  | 5384  | 4907  | 5839   | 5466   | 3751  |
|              |     | No. of Movements             | 440   | 336   | 348   | 331    | 380    | 387   |
|              |     | Movement Time (sec)          | 533   | 543   | 483   | 509    | 469    | 447   |
|              |     | Rest Time (sec)              | 1274  | 1283  | 1324  | 1297   | 1338   | 1360  |
|              |     | Vertical Activity            | 576   | 382   | 467   | 530    | 660    | 463   |
|              |     | No. of Vertical Movements    | 201   | 140   | 167   | 177    | 268    | 170   |
|              |     | Vertical Time (sec)          | 247   | 204   | 249   | 330    | 369    | 244   |
|              |     | Stereotypy Counts            | 2778  | 2395  | 2653  | 2741   | 2573   | 2681  |
|              |     | No. of Stereotypy            | 261   | 240   | 271   | 235    | 232    | 281   |
|              |     | Stereotypy Time (sec)        | 276   | 268   | 296   | 243    | 252    | 323   |
|              |     | Clockwise Revolutions        | 20    | 14    | 17    | 16     | 13     | 15    |
|              |     | Anticlockwise Revolutions    | 21    | 23    | 18    | 19     | 20     | 7     |
|              |     | Margin Time (sec)            | 1474  | 1530  | 1537  | 1530   | 1603   | 1486  |
|              |     | Center Time (sec)            | 325   | 269   | 262   | 269    | 196    | 333   |
|              |     | Left Front Corner Time (sec) | 214   | 160   | 145   | 296    | 159    | 155   |
|              |     | Right Front Corner Time (sec)| 245   | 200   | 348   | 110    | 171    | 192   |

TABLE 4a-continued

Group Y-1 Mouse Behavior Monitor Raw Data
Digiscan Animal Activity Monitor
Model RXYZCM(16), Omnitech Electronics, Columbus, OH

|  |  |  |  |  |  |  |  |  |
|---|---|---|---|---|---|---|---|---|
|  |  | Left Rear Corner Time (sec) | 197 | 154 | 136 | 187 | 290 | 150 |
|  |  | Right Rear Corner Time (sec) | 125 | 374 | 278 | 245 | 212 | 148 |
|  |  | Comments |  |  |  |  |  |  |

| Group | Day | Mouse I.D. | MK-2B | MK-3R | MK-4BR | MK-5RB | OK-1U | OK-2B |
|---|---|---|---|---|---|---|---|---|
|  |  | Person | Ed | Ed | Ed | Ed | Ed | Ed |
|  | 1 | Date | Dec. 4, 2001 | Dec. 5, 2001 | Dec. 5, 2001 | Dec. 5, 2001 | Dec. 4, 2001 | Dec. 5, 2001 |
|  |  | Start Time | 15:28 | 6:19 | 11:47 | 14:40 | 13:03 | 13:31 |
|  |  | Interval | 1 | 1 | 1 | 1 | 1 | 1 |
| Youkgong-dan |  | Horizontal Activity | 6557 | 6639 | 5753 | 4567 | 7618 | 6849 |
| 10 gm/kg |  | Total Distance (cm) | 3177 | 5011 | 3893 | 2783 | 5943 | 4899 |
|  |  | No. of Movements | 328 | 406 | 331 | 287 | 370 | 365 |
|  |  | Movement Time (sec) | 343 | 497 | 368 | 320 | 505 | 523 |
|  |  | Rest Time (sec) | 1483 | 1311 | 1439 | 1485 | 1301 | 1283 |
|  |  | Vertical Activity | 744 | 311 | 467 | 638 | 266 | 385 |
|  |  | No. of Vertical Movements | 216 | 145 | 156 | 153 | 121 | 118 |
|  |  | Vertical Time (sec) | 327 | 172 | 190 | 241 | 102 | 139 |
|  |  | Stereotypy Counts | 3176 | 2461 | 2296 | 1580 | 3311 | 3074 |
|  |  | No. of Stereotypy | 276 | 257 | 285 | 231 | 318 | 251 |
|  |  | Stereotypy Time (sec) | 355 | 287 | 269 | 207 | 369 | 337 |
|  |  | Clockwise Revolutions | 14 | 16 | 16 | 9 | 9 | 20 |
|  |  | Anticlockwise Revolutions | 7 | 15 | 14 | 6 | 28 | 19 |
|  |  | Margin Time (sec) | 1474 | 1509 | 1421 | 1677 | 1530 | 1326 |
|  |  | Center Time (sec) | 356 | 290 | 378 | 122 | 269 | 473 |
|  |  | Left Front Corner Time (sec) | 158 | 233 | 213 | 314 | 134 | 136 |
|  |  | Right Front Corner Time (sec) | 311 | 191 | 210 | 331 | 273 | 128 |
|  |  | Left Rear Corner Time (sec) | 116 | 154 | 107 | 104 | 256 | 194 |
|  |  | Right Rear Corner Time (sec) | 229 | 225 | 114 | 292 | 132 | 174 |

TABLE 4b

| Group | Day | Mouse I.D. | YC-1U | YC-2B | YC-3R | YC-4BR | YC-5RB | MC-1U | MC-2B |
|---|---|---|---|---|---|---|---|---|---|
|  |  | Person | Ed | Ed | Ed | Ed | Ed | Ed | Ed |
|  | 1 | Date | Dec. 4, 2001 | Dec. 4, 2001 | Dec. 5, 2001 | Dec. 5, 2001 | Dec. 5, 2001 | Dec. 4, 2001 | Dec. 4, 2001 |
|  | 1 | Start Time | 10:43 | 14:13 | 10:02 | 12:56 | 18:21 | 11:18 | 14:54 |
|  |  | Interval | 1 | 1 | 1 | 1 | 1 | 1 | 1 |
| Control |  | Horizontal Activity | 5320 | 8172 | 7785 | 7804 | 5813 | 6147 | 6373 |
|  |  | Total Distance (cm) | 3794 | 4858 | 6012 | 5988 | 3665 | 4175 | 4094 |
|  |  | No. of Movements | 241 | 383 | 425 | 382 | 309 | 364 | 413 |
|  |  | Move - Rest Time (sec) | −1094 | −878 | −826 | −854 | −1014 | −952 | −911 |
|  |  | Rest Time (sec) | 1449 | 1343 | 1317 | 1330 | 1410 | 1379 | 1360 |
|  |  | Vertical Activity | 331 | 554 | 757 | 763 | 282 | 490 | 403 |
|  |  | No. of Vertical Movements | 125 | 172 | 269 | 209 | 97 | 168 | 147 |
|  |  | Vertical Time (sec) | 160 | 273 | 310 | 327 | 164 | 224 | 177 |
|  |  | Stereotypy Counts | 1803 | 4090 | 2873 | 3279 | 2220 | 2501 | 2716 |
|  |  | No. of Stereotypy | 221 | 282 | 257 | 273 | 267 | 256 | 284 |
|  |  | Stereotypy Time (sec) | 204 | 402 | 272 | 315 | 253 | 268 | 321 |
|  |  | Clockwise Revolutions | 12 | 16 | 15 | 13 | 12 | 22 | 14 |
|  |  | Anticlockwise Revolutions | 15 | 14 | 19 | 27 | 15 | 6 | 15 |
|  |  | Margin - Center Time | 1491 | 1295 | 1238 | 1147 | 1393 | 971 | 925 |
|  |  | Center Time (sec) | 154 | 252 | 281 | 326 | 203 | 414 | 437 |
|  |  | Left Front Corner Time (sec) | 319 | 147 | 320 | 235 | 296 | 260 | 254 |
|  |  | Right Front Corner Time (sec) | 267 | 160 | 176 | 256 | 486 | 194 | 94 |
|  |  | Left Rear Corner Time (sec) | 245 | 166 | 202 | 223 | 101 | 147 | 120 |
|  |  | Right Rear - Corner Time | −119 | 262 | −46 | −56 | −98 | −82 | −50 |
|  |  | Comments |  |  |  |  |  |  |  |

| Group | Day | Mouse I.D. | MC-3R | MC-4BR | MC-5RB | OC-1U | OC-2B | OC-3R |
|---|---|---|---|---|---|---|---|---|
|  |  | Person | Ed | Ed | Ed | Ed | Ed | Ed |
|  | 1 | Date | Dec. 5, 2001 | Dec. 5, 2001 | Dec. 5, 2001 | Dec. 4, 2001 | Dec. 5, 2001 | Dec. 5, 2001 |
|  | 1 | Start Time | 9:27 | 12:22 | 15:14 | 11:53 | 10:38 | 15:47 |
|  |  | Interval | 1 | 1 | 1 | 1 | 1 | 1 |
| Control |  | Horizontal Activity | 7087 | 7125 | 6017 | 6721 | 6996 | 2226 |
|  |  | Total Distance (cm) | 5173 | 4226 | 4180 | 5524 | 5631 | 916 |
|  |  | No. of Movements | 443 | 389 | 320 | 365 | 354 | 158 |
|  |  | Move - Rest Time (sec) | −798 | −895 | −677 | −738 | −700 | −1541 |
|  |  | Rest Time (sec) | 1303 | 1351 | 1341 | 1272 | 1253 | 1672 |

TABLE 4b-continued

| | | | | | | | | |
|---|---|---|---|---|---|---|---|---|
| | | Vertical Activity | 595 | 545 | 580 | 310 | 490 | 25 |
| | | No. of Vertical Movements | 190 | 191 | 152 | 122 | 163 | 14 |
| | | Vertical Time (sec) | 242 | 267 | 285 | 139 | 167 | 13 |
| | | Stereotypy Counts | 2592 | 3416 | 2073 | 2554 | 3037 | 845 |
| | | No. of Stereotypy | 260 | 306 | 240 | 256 | 283 | 159 |
| | | Stereotypy Time (sec) | 260 | 385 | 232 | 294 | 315 | 152 |
| | | Clockwise Revolutions | 13 | 8 | 3 | 21 | 17 | 5 |
| | | Anticlockwise Revolutions | 22 | 20 | 20 | 15 | 27 | 2 |
| | | Margin - Center Time | 989 | 1241 | 1385 | 983 | 553 | 1739 |
| | | Center Time (sec) | 405 | 279 | 207 | 408 | 573 | 30 |
| | | Left Front Corner Time (sec) | 148 | 228 | 158 | 228 | 205 | 807 |
| | | Right Front Corner Time (sec) | 151 | 235 | 400 | 184 | 82 | 760 |
| | | Left Rear Corner Time (sec) | 160 | 201 | 119 | 153 | 143 | 27 |
| | | Right Rear - Corner Time | 45 | −18 | 50 | −28 | 73 | −433 |
| | | Comments | | | | | | cancer |

| Group | Day | Mouse I.D. | YK-1U | YK-2B | YK-3R | YK-4BR | YK-5RB | MK-1U |
|---|---|---|---|---|---|---|---|---|
| | | | Ed Dec. 4, 2001 | Ed Dec. 4, 2001 | Ed Dec. 5, 2001 | Ed Dec. 5, 2001 | Ed Dec. 5, 2001 | Ed Dec. 4, 2001 |
| | 1 | Start Time | 12:27 | 16:03 | 8:52 | 11:14 | 14:04 | 13:38 |
| | | Interval | 1 | 1 | 1 | 1 | 1 | 1 |
| Youkgong-dan | | Horizontal Activity | 7990 | 6767 | 7321 | 7087 | 7258 | 6015 |
| 10 gm/gk | | Total Distance (cm) | 5778 | 5384 | 4907 | 5839 | 5466 | 3751 |
| | | No. of Movements | 440 | 336 | 346 | 331 | 380 | 367 |
| | | Move - Rest Time (sec) | −741 | −720 | −841 | −768 | −669 | −913 |
| | | Rest Time (sec) | 1274 | 1263 | 1324 | 1297 | 1338 | 1360 |
| | | Vertical Activity | 576 | 362 | 467 | 530 | 860 | 463 |
| | | No. of Vertical Movements | 201 | 140 | 167 | 177 | 268 | 170 |
| | | Vertical Time (sec) | 247 | 204 | 249 | 330 | 369 | 244 |
| | | Stereotypy Counts | 2778 | 2395 | 2853 | 2741 | 2573 | 2661 |
| | | No. of Stereotypy | 261 | 240 | 271 | 235 | 232 | 281 |
| | | Stereotypy Time (sec) | 276 | 266 | 296 | 243 | 252 | 323 |
| | | Clockwise Revolutions | 20 | 14 | 17 | 18 | 13 | 15 |
| | | Anticlockwise Revolutions | 21 | 23 | 18 | 19 | 20 | 7 |
| | | Margin - Center Time | 1149 | 1261 | 1275 | 1261 | 1407 | 1133 |
| | | Center Time (sec) | 325 | 269 | 262 | 269 | 195 | 333 |
| | | Left Front Corner Time (sec) | 214 | 160 | 145 | 296 | 159 | 155 |
| | | Right Front Corner Time (sec) | 245 | 200 | 348 | 110 | 171 | 192 |
| | | Left Rear Corner Time (sec) | 197 | 154 | 138 | 187 | 290 | 150 |
| | | Right Rear - Corner Time | −94 | 203 | 68 | 47 | 5 | −18 |
| | | Comments | | | | | | |

| Group | Day | Mouse I.D. | MK-2B | MK-3R | MK-4BR | MK-5RB | OK-1U | OK-2B |
|---|---|---|---|---|---|---|---|---|
| | | | Ed Dec. 4, 2001 | Ed Dec. 5, 2001 | Ed Dec. 5, 2001 | Ed Dec. 5, 2001 | Ed Dec. 4, 2001 | Ed Dec. 5, 2001 |
| | 1 | Start Time | 15:28 | 6:19 | 11:47 | 14:40 | 13:03 | 13:31 |
| | | Interval | 1 | 1 | 1 | 1 | 1 | 1 |
| Youkgong-dan | | Horizontal Activity | 6557 | 6839 | 5753 | 4567 | 7618 | 6849 |
| 10 gm/gk | | Total Distance (cm) | 3177 | 5011 | 3893 | 2783 | 5943 | 4899 |
| | | No. of Movements | 328 | 406 | 331 | 287 | 370 | 385 |
| | | Move - Rest Time (sec) | −1120 | −814 | −1071 | −1165 | −796 | −760 |
| | | Rest Time (sec) | 1483 | 1311 | 1439 | 1485 | 1301 | 1283 |
| | | Vertical Activity | 744 | 311 | 467 | 538 | 266 | 365 |
| | | No. of Vertical Movements | 216 | 145 | 168 | 153 | 121 | 118 |
| | | Vertical Time (sec) | 327 | 172 | 190 | 241 | 102 | 139 |
| | | Stereotypy Counts | 3176 | 2461 | 2298 | 1580 | 3311 | 3074 |
| | | No. of Stereotypy | 276 | 257 | 265 | 231 | 316 | 251 |
| | | Stereotypy Time (sec) | 355 | 267 | 269 | 207 | 369 | 337 |
| | | Clockwise Revolutions | 14 | 16 | 16 | 9 | 9 | 20 |
| | | Anticlockwise Revolutions | 7 | 16 | 14 | 5 | 28 | 19 |
| | | Margin - Center Time | 1118 | 1219 | 1043 | 1555 | 1261 | 853 |
| | | Center Time (sec) | 356 | 290 | 378 | 122 | 269 | 473 |
| | | Left Front Corner Time (sec) | 156 | 233 | 213 | 314 | 134 | 138 |
| | | Right Front Corner Time (sec) | 311 | 191 | 210 | 331 | 273 | 128 |
| | | Left Rear Corner Time (sec) | 118 | 154 | 107 | 104 | 258 | 194 |
| | | Right Rear - Corner Time | 34 | 32 | −63 | 42 | −89 | 21 |

In Tables 4a and 4b, Mouse I.D. represents a mouse ID, Person represents an experimenter, Interval represents a time interval, Horizontal Activity represents a horizontal activity, a Total Distance represents a total distance, No. of Movement represents a number of movement, Rest Time represents a rest time, Vertical Activity represents a vertical activity, No. of Vertical Movement represents a number of vertical movement, Vertical Time represents a vertical time, Stereotypy Counts represents a stereotypy counts, No. of Stereotypy represents number of times the monitor observes stereotypic behavior, Stereotypy Time represents total amount of time that stereotypic behavior is exhibited, Clockwise Revolutions represents clockwise revolutions, Anticlockwise Revolutions represents anticlockwise revolutions, Margin Time represents a margin time, Center Time represents a center time, Left Front Corner Time represents time spent by the animal moves from left to front, Right Front Corner Time represents time spent by the animal moves from right to front, Left Rear Corner Time represents time spent by the animal moves from left to rear, and Right Rear Corner Time represents time spent by the animal moves from right to rear.

At this time, stereotypy refers to the symptom that repetitive, stereotypic behavior is continuously exhibited.

Figure 9:
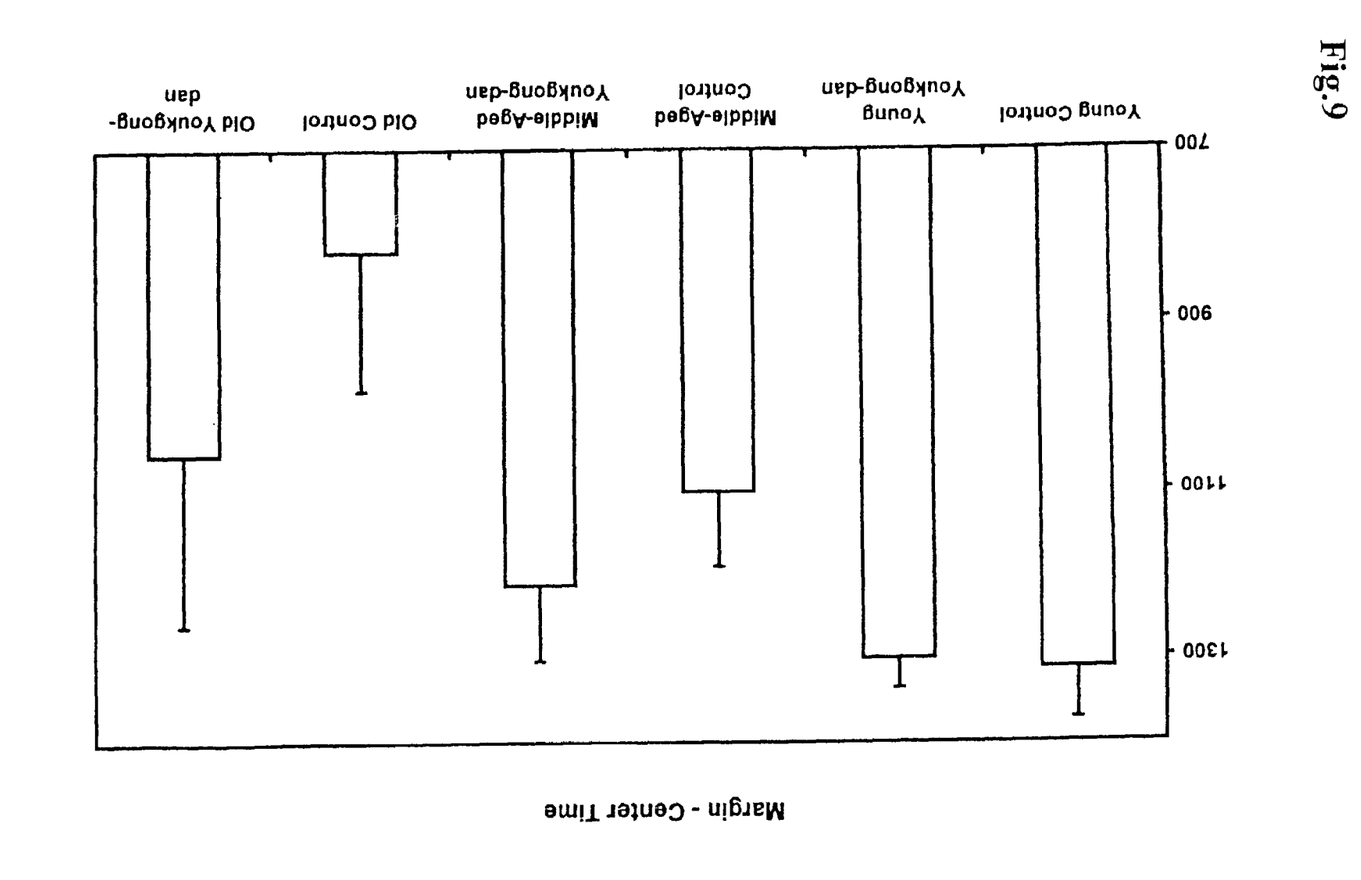
FIG. 9 is a view showing open field locomotor behavior data for open field margin minus center time of 5 months (young group), 17 months (middle-aged group) and 28 months (old group) mice, either were controlled or were fed with the fatigue recovery medicine for changing in hepatic mRNA levels of stress-related genes or were controlled in accordance with the preferred embodiment of the present invention.

FIG. 9 is a view showing open field locomotor behavior data for open field margin minus center time of 5 months (young group), 17 months (middle-aged group) and 28 months (old group) mice, either were controlled or were fed with the fatigue recovery medicine for changing in hepatic mRNA levels of stress-related genes or were controlled in accordance with the preferred embodiment of the present invention.

The difference in time a mouse spends at the margin of the enclosure minus the time it spends in the center is a measure of exploratory behavior (FIG. 9). This measure decreased with age, but the fatigue recovery medicine tended to increase it in old animals. Other measures of behavior did not show significant changes.

Therefore, the fatigue recovery medicine for changing in hepatic mRNA levels of stress-related genes in accordance with the embodiment of the present invention is very effective in treating illness such as chronic fatigue, neurasthenia, anxiety neurosis, aging, memory power reduction, etc.

While the invention has been shown and described with reference to certain preferred embodiments thereof, it will be understood by those skilled in the art that various changes in form and details may be made therein without departing from the spirit and scope of the invention as defined by the appended claims.

As described above, by the administration of the fatigue recovery medicine for changing in hepatic mRNA levels of stress-related genes of the present invention, when measuring the basal levels of expression of mRNA of 23 stress-related genes, seven of these genes showed measurable expression levels: Gadd45, Grp78, Hsp86, Mdm2, Sod1, and Trpm2. Thus, the medicine is very effective in treating illness such as chronic fatigue, neurasthenia, anxiety neurosis, aging, memory power reduction, etc.

What is claimed is:

1. A fatigue recovery medicine for changing in hepatic mRNA levels of stress-related genes, which is composed of: astragali radix of 13.2% by weight, atractylodis rhizoma alba of 8.8% by weight, angelicae gigantis radix of 8.8% by weight, longanae arillus of 8.8% by weight, lycii folium of 8.8% by weight, cridii rhizoma of 6.7% by weight, glycyrrhizae radix of 4.4% by weight, carthami flos of 4.4% by weight, cervi parvum cornu of 4.4% by weight, crataegi fructus of 4.4% by weight, rehmanniae radix preparata of 4.4% by weight, saussureae radix of 4.4% by weight, amomi fructus of 4.4% by weight, polygony multiflori radix of 4.4% by weight, paeoniae radix alba of 4.4% by weight and ginseng radix of 4.4% by weight.

* * * * *